United States Patent [19]

Takagishi et al.

[11] 4,405,597

[45] Sep. 20, 1983

[54] MEDICAMENT CAPSULES FOR RECTAL APPLICATION

[75] Inventors: Yasushi Takagishi, Nishinomiya; Yoshio Doi, Ibaraki; Kiichiro Ohsuga, Kusatsu; Noboru Hoshi, Higashi-kurume, all of Japan; Shionogi & Co., Ltd., 03, Osaka, both of Japan

[73] Assignee: Shin-Etsu Chemical Co., Ltd., Tokyo

[21] Appl. No.: 292,040

[22] Filed: Aug. 11, 1981

[30] Foreign Application Priority Data

Feb. 24, 1981 [JP] Japan ................................. 56-26624

[51] Int. Cl.³ ......................... A61K 9/48; A61K 9/36
[52] U.S. Cl. .................................................... 424/35
[58] Field of Search ....................... 424/14, 16, 21, 35, 424/37

[56] References Cited

U.S. PATENT DOCUMENTS

| | | | |
|---|---|---|---|
| 3,197,369 | 7/1965 | Widmann et al. | 424/37 |
| 3,444,290 | 5/1969 | Wai | 424/37 |
| 3,467,748 | 9/1969 | Widmann | 424/37 |
| 3,656,997 | 4/1972 | Cordes | 424/35 |
| 4,111,201 | 9/1978 | Theewes | 424/19 |
| 4,111,202 | 9/1978 | Theewes | 424/19 |
| 4,111,203 | 9/1978 | Theewes | 424/19 |
| 4,160,020 | 7/1979 | Ayer et al. | 424/19 |
| 4,226,981 | 10/1980 | Onda et al. | 424/35 |
| 4,265,875 | 5/1981 | Byrne et al. | 424/35 |
| 4,278,633 | 7/1981 | Fujii | 424/37 |
| 4,339,463 | 7/1982 | Takagishi et al. | 424/35 |

*Primary Examiner*—Shep K. Rose
*Attorney, Agent, or Firm*—Toren, McGeady and Stanger

[57] ABSTRACT

The invention provides a novel means for the administration of a therapeutically effective ingredient in the form of a rectally applicable medicament capsule, in which the otherwise unavoidable extreme variation in the absorbability of the effective ingredient among the individuals rectally treated with the capsules is minimized. It has been unexpectedly found that, when the effective ingredient is contained in the capsule in the form of a liquid medicine, the osmotic pressure of the liquid content plays a very essential role in the absorption of the effective ingredient through the rectum and the variation in the absorbability of the effective ingredient among the individuals can be minimized when the osmotic pressure of the liquid content is substantially higher than the osmotic pressure of the rectal fluid with which the capsules are contacted.

2 Claims, 5 Drawing Figures

MEDICAMENT CAPSULES FOR RECTAL APPLICATION

BACKGROUND OF THE INVENTION

The present invention relates to a novel medicament capsule for rectal application. More particularly, the invention relates to a medicament form of a hard capsule containing a therapeutically effective ingredient capable of being absorbed through the rectum, of which the releasability of the effective ingredient is markedly improved.

As is well known, a variety of medicines are used in a medicament form suitable for rectal application with an object either to obtain a systemic action or to obtain a local action of the effective ingredient. Several of the examples of the medicines of which a systemic action is desired by the rectal application include antipyretic, anodynic and antiphlogistic agents such as aspirin, aminopyrin, sulpyrin, phenylbutazone, oxyphenbutazone, indomethacin and the like, antispasmodic agents such as butylscopolamine bromide and the like, antibiotics such as erythromycin and the like, antituberculosis agents such as ethionamide and the like, and others. Those medicines of which a local action is desired include, on the other hand, astringents, local anesthetics and bactericidal agents with or without admixture of an adrenocortical hormone for haemorrhoids.

At any rate, the effective ingredient in the medicine administrated by rectal application is directly absorbed in the venous plexus of the rectum to be distributed thoughout the body by the blood circulation without passing the portal vein and the liver. Therefore, a rectally applicable medicament form is preferable particularly for the medicines of which the effective ingredient causes a disorder in the stomach when orally administrated or the ingredient is susceptible to decomposition in the digestive tract or in the liver resulting in decreased effectiveness of the medicine.

As is well known, the medicament forms for rectal application in general include suppositories and so-called rectal capsules.

Suppositories as a medicament form are prepared usually by dispersing the therapeutically active ingredient in a base such as cacao butter, polyethyleneglycol, mixture of higher fatty acid glycerides and the like solidifying and shaping the blend into a desired form, e.g. a conical or cannonball-like form, suitable for insertion into the coelom through the anus. Suppositories are the most widely used medicament form for rectal application and effective by releasing the effective ingredient in the rectum when melted at the body temperature or dissolved in the rectal fluid.

Suppositories present a very convenient means for rectal application of the medicine but not without various problems in the preparation and storage thereof. Several of the problems are that an efficient means is required for the uniform dispersion of the effective ingredient in the highly consistent suppository base, that suppositories are not a suitable medicament form for an ingredient susceptible to thermal decomposition because the ingredient must be distributed in the base molten by heating, that suppositories must be stored in a cool place because deformation of suppositories is unavoidable at a relatively high temperature and that specific facilities are necessary for the preparation thereof to be in compliance with the aforementioned problems.

On the other hand, a rectal capsule is a modification of the suppository in a sense and can be prepared in a manner similar to the preparation of soft capsules. That is, the therapeutically effective ingredient, alone or with admixture of other additives according to need, is shaped by lightly compressing and encapsulated and further shaped with a capsule base such as gelatin. Therefore, preparation of rectal capsules also requires specific facilities and skillful works.

In view of the above problems in the rectal capsules, it is another possible way to utilize an ordinary gelatin-made capsule for oral administration as the medicament form for rectal application. Several difficulties are, however, encountered in the use of gelatin capsules for rectal application. For example, medicines with acidity or in a liquid form cannot be encapsulated in both hard and soft gelatin-made capsules. Further, powdery medicines encapsulated in soft capsule are not free from the problem in the stability in addition to the burdensomeness in the preparation of the medicament form.

In view of the above problems in the medicament forms suitable for rectal application, the inventors have come to the idea of utilizing hard capsules shaped of an enterosoluble material for the medicament form for rectal application. Their investigations along this line have led to the discovery of an excellent enterosoluble material suitable for rectal application in the form of a hard capsule. An enteric material has been proposed which is a cellulose ether derivative which is a mixed ester of an alkylcellulose, hydroxyalkylcellulose or hydroxyalkyl alkylcellulose esterified with acidic succinyl groups and aliphatic monoacyl groups, e.g. acetyl groups. These materials are disclosed in U.S. patent application Ser. No. 140,478, filed Apr. 15, 1980 and thus it is known how to make such materials. The hard capsules shaped of the above mentioned cellulose derivative have excellent enteric solubility, intoxicity to the human body and stability with the elapse of time. Further, the capsules have sufficient pliability even without formulating a plasticizer and their disintegrability and smoothness on the surface permit their application as a medicament capsule for rectal application. In addition, the capsules shaped of the above mentioned cellulose derivative can be filled with any aqueous medicine in the form of an aqueous solution, aqueous suspension or emulsion so that a great advantage is obtained in the versatility of the medicines filling the capsule in comparison with other medicament forms.

In extending the investigations with the medicament capsules for rectal application formed of the hard capsule shells of the cellulose derivative, a very serious problem was encountered that the disintegrability of the capsules and the releasability of the effective ingredient contained in the capsule in the rectum are widely diversified among the individuals administrated with the medicament capsules by rectal application so that an extremely large difference was found in the concentration of the effective ingredient in the blood.

SUMMARY OF THE INVENTION

It is therefore an object of the present invention to provide a medicament capsule suitable for rectal application containing an effective ingredient capable of being absorbed through the rectum, with which the releasability of the effective ingredient and hence the absorbability of the ingredient are quite uniform among the individuals administrated with the capsules by rectal application.

The medicament capsule for rectal application according to the present invention comprises a hard capsule shell and a therapeutically effective ingredient capable of being absorbed through the rectum contained in the hard capsule shell in the form of an aqueous liquid medicine, the osmotic pressure of said liquid medicine being substantially higher than the osmotic pressure of the rectal fluid.

The hard capsule shell is preferably shaped of the above described mixed ester of a cellulose ether and, by so controlling the osmotic pressure of the liquid content, a remarkable uniformity is obtained in the absorbability of the effective ingredient among the individuals administrated with the capsules by rectal application.

DETAILED DESCRIPTION OF THE PREFERRED EMBODIMENTS

Figure 1:
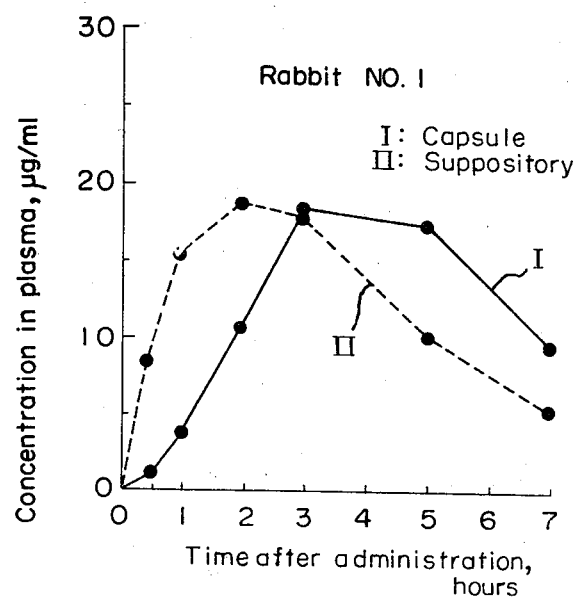
FIGS. 1 to 4 show the change in the concentration of sulfamethoxazole in the blood plasma of rabbits administrated by rectal application with the medicine in the form of the medicament capsule containing the same, of which the osmotic pressure of the content is 20 m Osm/kg H$_2$O, as a function of time.

The hard capsule shells used for the inventive medicament capsules for rectal application are preferably shaped of the mixed ester of the cellulose ether as is mentioned above although the principle of the present invention consisting in the control of the osmotic pressure of the liquid content in the capsule is not limited to the capsules made of such a cellulose derivative.

The enteric cellulose derivative for shaping the shells of the inventive medicament capsules is a mixed ester of an alkylcellulose, hydroxyalkylcellulose or hydroxyalkyl alkylcellulose esterified with acidic succinyl groups and aliphatic monoacyl groups such as acetyl and propionyl groups and is described in detail, for example, in U.S. Pat. No. 4,226,981. Several remarkable advantages are obtained by the use of the cellulose derivatives of this type as a material for shaping the capsule shells of the inventive medicament capsules for rectal application.

Despite the advantages obtained with the medicament capsules for rectal application, the inventors have become aware of the very much diversified effectiveness of the administration when a number of test animals are rectally treated. That is, when a capsule containing either an aqueous or oleic medicine is rectally applied to a test animal such as rabbits, the disintegrability of the capsule in the rectum and the absorbability of the effective ingredient through the rectum are widely diversified from individual to individual to an extent beyond imagination.

To demonstrate the above mentioned diversity in the effectiveness of the rectal application among individual test animals, dose tests were undertaken with several rabbits with sulfamethoxazole as the test ingredient.

Thus, several hard capsule shells of No. 0 size having a wall thickness of about 100 μm each weighing 110 mg were prepared by the dipping method from a mixed ester of a hydroxypropyl methylcellulose esterified with succinic anhydride and acetic anhydride to give degrees of substitution of the acidic succinyl groups and the acetyl groups of 0.25 and 0.57, respectively, per glucose unit. Each of the capsule shells was filled with an aqueous solution of 70 mg of sulfamethoxazole in 600 mg of a 0.001 N hydrochloric acid containing 2% by weight of a hydroxypropylcellulose. For comparison, suppositories were prepared, each being shaped of 930 mg of Witepsol, a mixture of mono-, di- and triglycerides of fatty acids, as the suppository base and 70 mg of sulfamethoxazole uniformly dispersed in the base.

Each one of the above prepared medicament capsules or the suppositories was inserted to the rectum about 3 cm deep from the anus of one of the male rabbits No. 1 to No. 7 having a body weight of 2.9 to 3.1 kg after a fasting period of 17 hours and the concentration of the sulfamethoxazole in the blood plasma was determined by periodically taking the blood from the earlobe of the rabbit followed by centrifugal separation of the plasma. The results are shown in FIGS. 1 to 4, of which FIGS. 1 to 3 give a comparison between the medicament capsule and the suppository in the rabbits No. 1, No. 2 and No. 3, respectively, the solid line being for the capsules and the broken line being for the suppositories and FIG. 4 gives the results with the capsules in the rabbits No. 4 to No. 7 by the curves IV to VII, respectively.

Figure 2:
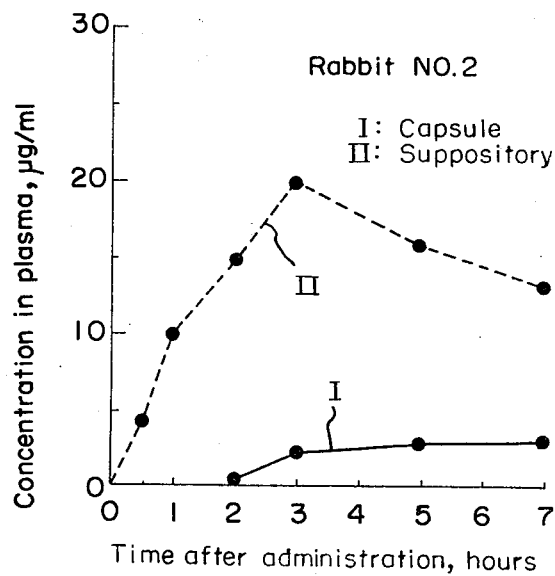
Figure 3:
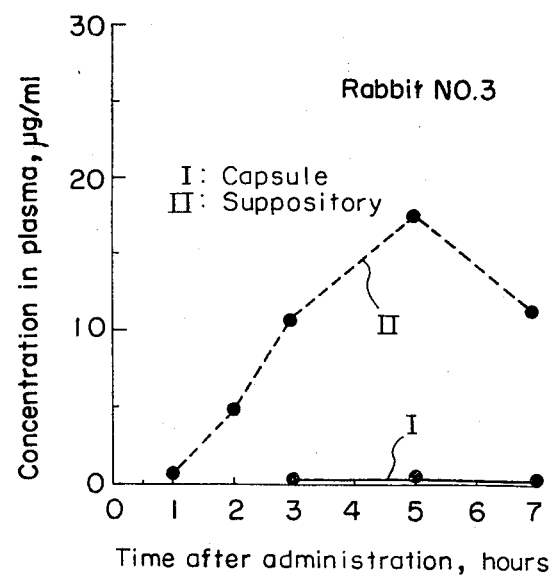
Figure 4:
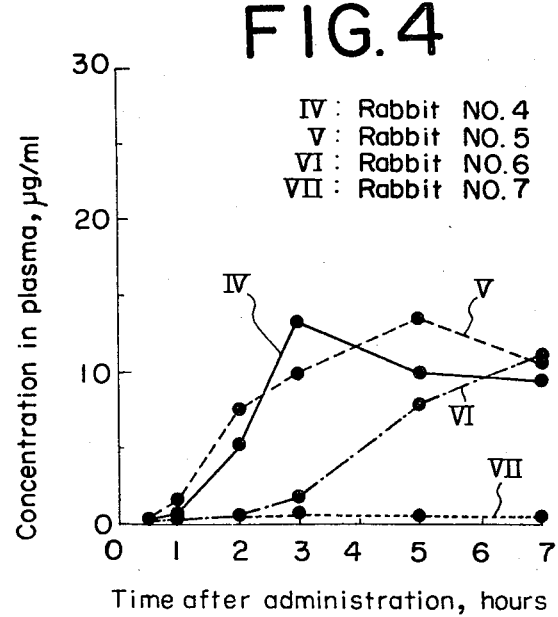

As is shown in FIG. 1, the velocities of absorption for the capsule and the suppository were about the same in the rabbit No. 1 while the velocities were widely different in the rabbits No. 2 and No. 3 as is clear from FIGS. 2 and 3. FIG. 4 more clearly indicates the dependency of the absorbability of a medicine on individuals in the rectal application of medicament capsules. Although differences among individuals may be not surprising since the disintegration of the capsule and absorption of the effective ingredient should be influenced by the amount of the rectal fluid and the value of pH thereof, the extraordinarily large difference, for example, between the rabbit No. 1 and the rabbit No. 2, No. 3 or No. 7 had been quite out of imagination before the tests.

As a result of the investigations directed to solve the above described problem of non-uniformity of the absorption of effective ingredients contained in the rectally applied medicament capsules among individuals, a conclusion has been arrived at that the value of the osmotic pressure of the aqueous liquid medicine contained in the capsule plays a very important role on the disintegration of a rectally applied capsule in a living body and, consequently, on the release of the effective ingredient contained in the capsule.

Further investigations undertaken by the inventors have established that the osmotic pressure of the liquid medicine contained in the capsule should be substantially higher than that of the body fluid or, in particular, the rectal fluid so that the disintegration of the capsule is uniformly accelerated without being affected by the fluctuating living body conditions since the rectal fluid is positively taken into the capsule through the capsule walls and, as a consequence, the difference in the absorbability of the effective ingredient through the rectum is minimized among individuals to overcome the above described serious problem encountered in the dose tests with rabbits as the test animals.

It is known that the osmotic pressure of human body fluids or, in particular, the rectal fluid is usually in the range from 280 to 300 m Osm/kg H$_2$O. Therefore, the osmotic pressure of the liquid medicine contained in the rectally applicable medicament capsule should be kept substantially higher than above. It should be noted, however, that a liquid medicine having an excessively high osmotic pressure may cause diarrhea when administrated rectally so that the osmotic pressure should be controlled within a range from 350 to 2000 m Osm/kg $H_2O$ or, preferably, in the range from 500 to 1600 m Osm/kg $H_2O$. Meanwhile, the osmotic pressure of the content of the rectally applied capsules in the above described dose tests demonstrated in FIGS. 1 to 4 was about 20 m Osm/kg $H_2O$.

The osmotic pressure of the liquid content can be freely controlled by adding a suitable amount of an osmosis adjustment agent to the content of the capsule. Such an osmosis adjustment agent must satisfy several requirements (a) that the capsule shell is not affected thereby, (b) that the liquid content can be made sufficiently hypertonic by the addition of a small amount thereof, and (c) that it is not irritative to the mucous membrane of the rectum not to cause diarrhea. Therefore, the osmosis adjustment agent should be selected with consideration of these requirements. Several of the examples of preferred osmosis adjustment agents are inorganic salts such as sodium chloride, potassium chloride, ammonium chloride and the like and organic compounds such as glucose, fructose, sorbitol, xylitol, mannitol, glycerin, low-molecular dextran and the like.

The amount of the osmosis adjustment agent to be added to the liquid content of the capsule is usually in the range from 1 to 20% by weight in the case of the inorganic salts above mentioned and from 5 to 30% by weight in the case of the above mentioned organic compounds. The amount should be sufficient to make the liquid content of the capsule more hypertonic than the rectal fluid while an excessive amount of the osmosis adjustment agent is undesirable in several respects with a too high osmotic pressure of the liquid content of the capsule in addition to the difficulty in introducing the agent into the capsule.

It should be noted that there are cases where the amount of addition of the osmosis adjustment agent is limited by the solubility thereof even within the above mentioned ranges. An auxiliary means in such a case is the replacement of a part of the above mentioned osmosis adjustment agent with different kinds of additives such as a salt of an organic acid, e.g. potassium citrate, potassium acetate, potassium gluconate and the like in an amount of 1 to 10% by weight and/or an acidic amino acid or a derivative thereof, e.g. glutanim, glutamic acid, asparagine, aspartic acid and the like in an amount of 0.1 to 1% by weight.

In the inventive medicament capsules, the pH value of the content of the capsule should be kept in the range from 3 to 4 in order to ensure stability of the capsule shells so that it is sometimes undertaken to add a small amount of hydrochloric acid to the content of the capsule according to need. When the pH is too high above 4, the stability of the capsule shell formed of the enteric cellulose derivative is decreased while an excessively acidic content is undesirable due to the increased irritation to the mucous membrane of the rectum.

Further, the liquid content of the inventive medicament capsule may be admixed with various kinds of additives according to need depending on the properties of the content which may be an aqueous solution, suspension in water or in oil, aqueous emulsion and the like. For example, carboxymethylcellulose, hydroxypropylcellulose, polyvinyl pyrrolidone, propyleneglycol, gum arabic and gum tragacanth as well as fatty acid esters of sucrose, polyoxyethylene derivatives of castor oil, bile acid and salts thereof and the like may be added either alone or in combination of two kinds or more as a thickening agent, dispersing agent or suspending agent in accordance with the particular object.

The above described control of the osmotic pressure of the liquid content of the inventive medicament capsule for rectal application is very effective in that, with the liquid content of the capsule kept more hypertonic than the rectal fluid, the disintegration of the capsule is accelerated with minimum influence of the variation factors in the living body so that the release velocity of the effective ingredients in the capsule is increased uniformly among the individuals resulting in the enhancement of the bioavailability of the medicine with very much decreased variations among the individual patients.

Following are the results of the experiments undertaken with an object to demonstrate the effectiveness of the osmotic pressure control with rabbits as the test animals.

EXAMPLE 1

Figure 5:
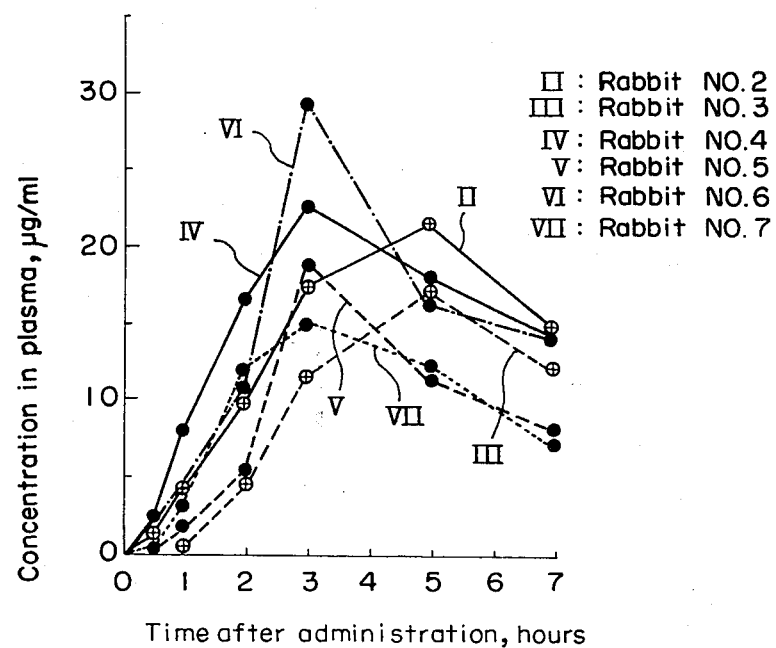
FIG. 5 shows the change in the concentration of sulfamethoxazole in the blood plasma of rabbits administrated by rectal application with the medicine in the form of the medicament capsule containing the same, of which the osmotic pressure of the content is 580 m Osm/kg H$_2$O, as a function of time.

Medicament capsules were prepared with the same hard capsule shells as used in the above described comparative tests with the rabbits No. 1 to No. 7, each capsule containing 70 mg of sulfamethoxazole, 12 mg of sodium chloride and 588 mg of a solution containing 2% by weight of a hydroxypropylcellulose in a 0.001 N hydrochloric acid. The osmotic pressure of the liquid content of the capsules was 580 m Osm/kg $H_2O$. These capsules were applied to several rabbits rectally and the concentration of the effective ingredient in their blood plasma was followed over a length of time in the same manner as before to give the results plotted in FIG. 5.

As is clear from this figure, the absorption of the effective ingredient was remarkably improved in the test rabbits No. 2 and No. 3 which showed very poor absorption in the comparative tests shown in FIGS. 2 and 3, respectively. This effect was especially remarkable in the rabbit No. 3. Generally speaking, the absorbability of the effective ingredient administrated with the inventive capsules with controlled osmotic pressure was at about the same level as in the administration in the form of suppositories. It was noted that the absorption of the effective ingredient in the rabbits No. 4 to No. 7 was also improved in comparison with the results shown in FIG. 4 with less variation among the rabbits.

No adverse side effects such as irritation and diarrhea were observed in the irritation test for the rabbit rectum by the addition of sodium chloride to the capsule content.

EXAMPLE 2

Medicament capsules were prepared in the same manner as above, each capsule containing 70 mg of sulfamethoxazole, 2 mg of gum tragacanth, 125 mg of glucose and 473 mg of 0.001 N hydrochloric acid. The osmotic pressure of the liquid content of the capsules was 1350 m Osm/kg $H_2O$.

The capsules were rectally applied to several rabbits and the absorption of the effective ingredient was examined by the concentration of it in the blood plasma in the same manner as in Example 1. The absorption of the effective ingredient was apparently improved by the addition of glucose as an osmosis adjustment agent.

In the following Examples 3 to 9, only the formulation of the content of the capsule and the osmotic pressure of the liquid content in each of the tests are given here, although the tests were undertaken by preparing the medicament capsules in the same manner as in Example 1 and the results of the absorption of the effective ingredient were as good as in the preceding Examples.

EXAMPLE 3

| | | |
|---|---|---|
| Sulfamethoxazole | 70 | mg/capsule |
| Sodium chloride | 30 | |
| Glutamic acid | 6 | |
| Propyleneglycol | 6 | |
| Distilled water | 558 | |
| Total | 670 | |
| Osmotic pressure | 1570 | m Osm/kg H$_2$O |

EXAMPLE 4

| | | |
|---|---|---|
| Chlorpromazine hydrochloride (tranquilizer) | 10 | mg/capsule |
| Ascorbic acid | 1 | |
| 5% Sodium chloride solution in 0.001 N hydrochloric acid | 599 | |
| Total | 610 | |
| Osmotic pressure | 1590 | m Osm/kg H$_2$O |

EXAMPLE 5

| | | |
|---|---|---|
| Dicethiamine hydrochloride (vitamin) | 50 | mg/capsule |
| 5% Sodium chloride solution in 0.001 N hydrochloric acid | 600 | |
| Total | 650 | |
| Osmotic pressure | 1600 | m Osm/kg H$_2$O |

EXAMPLE 6

| | | |
|---|---|---|
| Vinblastine sulfate (anti-tumor agent) | 5 | mg/capsule |
| Sodium laurylsulfate | 5 | |
| 5% Sodium chloride solution in 0.001 N hydrochloric acid | 600 | |
| Total | 610 | |
| Osmotic pressure | 1610 | m Osm/kg H$_2$O |

EXAMPLE 7

| | | |
|---|---|---|
| Acetaminophen (antipyretic and anodynic agent) | 100 | mg/capsule |
| Glucose | 120 | |
| Glutamic acid | 5 | |
| Distilled water | 400 | |
| Total | 625 | |
| Osmotic pressure | 1380 | m Osm/kg H$_2$O |

EXAMPLE 8

| | | |
|---|---|---|
| Dextromethorphan hydrobromide (antitussive agent) | 2 | mg/capsule |
| Glutamic acid | 5 | |
| 5% Aqueous sodium chloride solution | 598 | |
| Total | 605 | |
| Osmotic pressure | 1600 | m Osm/kg H$_2$O |

EXAMPLE 9

| | | |
|---|---|---|
| Chlorpheniramine maleate (antihistaminic agent) | 10 | mg/capsule |
| Glucose | 130 | |
| 0.001 N Hydrochloric acid | 500 | |
| Total | 640 | |
| Osmotic pressure | 1460 | m Osm/kg H$_2$O |

What is claimed is:

1. A method for the administration of a rectally absorbable, therapeutically effective ingredient which comprises inserting into the rectum through the anus a medicament capsule formed of a hard capsule shell made of an enterosoluble material selected from the group consisting of mixed esters of an alkylcellulose, a hydroxyalkylcellulose or a hydroxyalkyl alkylcellulose esterified with acidic succinyl groups and aliphatic monoacyl groups, and encapsulating a liquid content containing the rectally absorbable, therapeutically effective ingredient, the osmotic pressure of the liquid content being substantially higher than the osmotic pressure of the rectal fluid.

2. The process of claim 1 wherein the liquid content has a pH value in the range from 3.0 to 4.0.

* * * * *

UNITED STATES PATENT AND TRADEMARK OFFICE
CERTIFICATE OF CORRECTION

PATENT NO. : 4,405,597
DATED : Sept. 20, 1983
INVENTOR(S) : Yasushi Takagishi, et al It is certified that error appears in the above-identified patent and that said Letters Patent is hereby corrected as shown below:

In the heading in the patent [75] and [73] should read as follows:

[75] Inventors: --Yasushi Takagishi, Nishinomiya; Yoshio Doi, Ibaraki; Kiichiro Ohsuga, Kusatsu; Noboru Hoshi, Higashi-kurume, all of Japan --

[73] Assignee: --Shin-Etsu Chemical Co., Ltd., and Shionogi & Co., Ltd., of Tokyo, Japan--

Signed and Sealed this

Twenty-first Day of February 1984

[SEAL]

Attest:

GERALD J. MOSSINGHOFF

Attesting Officer

Commissioner of Patents and Trademarks